United States Patent [19]

Mango

[11] 4,163,019
[45] Jul. 31, 1979

[54] PRODUCTION OF 4,4'-ALKYLIDENE DIPHENYL DIISOCYANATE

[75] Inventor: Frank D. Mango, Houston, Tex.

[73] Assignee: Shell Oil Company, Houston, Tex.

[21] Appl. No.: 922,903

[22] Filed: Jul. 10, 1978

[51] Int. Cl.² ............... C07C 118/00; C07C 119/048; C07C 125/06
[52] U.S. Cl. .................. 260/453 P; 260/453 AM; 560/24; 560/25
[58] Field of Search ................ 260/453 P, 453 AM

[56] References Cited

U.S. PATENT DOCUMENTS

| | | | |
|---|---|---|---|
| 3,059,021 | 10/1962 | Prill | 560/25 |
| 3,243,448 | 3/1966 | Erner | 260/453 P |
| 3,277,098 | 10/1966 | Merten | 546/108 |
| 3,345,395 | 10/1967 | Muller et al. | 260/453 P |
| 3,719,699 | 3/1973 | McClure et al. | 260/453 PC |

OTHER PUBLICATIONS

Kirk–Othmer, "Encyclopedia of Chemical Technology", Second Edition, vol. 12, pp. 53–59.
*Chemical Week,* Nov. 9, 1977, pp. 57–58.
Wagner, *J. Org. Chem.,* vol. 59, pp. 1862–1881 (1959).

*Primary Examiner*—Dolph H. Torrence

[57] ABSTRACT

A process for the production of 4,4'-methylene diphenyl diisocyanate (4,4'-MDI) to the substantial exclusion of other position isomers and of higher oligomers comprises a coupling reaction in which formaldehyde is condensed with an N-phenyl alkylcarbamate under mild conditions to produce the dialkyl carbamate of 4,4'-methylene diphenyl diisocyanate, and a catalytic exchange reaction in which the latter is reacted with phenyl isocyanate to produce with extremely high selectivity 4,4'-methylene diphenyl diisocyanate as product and N-phenyl alkylcarbamate which is recycled to the coupling reaction. In the overall process, formaldehyde and phenyl isocyanate are selectively converted to 4,4'-MDI. By substituting a higher aldehyde or a ketone for formaldehyde, the process may also be employed to produce other 4,4'-alkylidene diphenyl diisocyanates.

10 Claims, 1 Drawing Figure

PRODUCTION OF 4,4'-ALKYLIDENE DIPHENYL DIISOCYANATE

BACKGROUND OF THE INVENTION

1. Field of the Invention

This invention is directed to a process for the selective production of 4,4'-alkylidene diphenyl diisocyanates and specifically 4,4'-methylene diphenyl diisocyanate, to the exclusion of other isomers and oligomers.

2. Description of the Prior Art

Organic isocyanates are materials of commerce employed in the production of polyurethane resins. Of increasing commercial importance are the polymethylene polyphenyl isocyanates, referred to as PMPPI. One member of the PMPPI family, 4,4'-methylene diphenyl diisocyanate, referred to in the industry as 4,4'-MDI, is especially desirable because it exhibits outstanding properties in polyurethanes.

The prior art with respect to production of isocyanates, both as to methods for their chemical synthesis and as to their commercial production, is summarized in Kirk-Othmer, "Encyclopedia of Chemical Technology", Second Edition, Volume 12, pages 53 et seq. Under the heading of Manufacture, it is stated that:

"The reaction of amines with phosgene, commonly referred to as phosgenation, is, for economic reasons, used almost exclusively for the manufacture of isocyanates . . . Because of the several side reactions and associated complications, the development of practical, high-yield reaction conditions has been studied extensively and many patents have been issued covering detailed procedures . . .

"The problems are multiplied in the manufacture of a diisocyanate, where the simple by-products may be intermolecular, e.g., a mixed carbamyl chloride/amine hydrochloride, and the urea by-product may be polymeric.

"It appears that all commercial manufacturing processes for aromatic isocyanates have the following approach: (1) The solution of an amine in an aromatic solvent . . . is mixed with a solution of phosgene in the same solvent at a temperature below 60°; (2) the resulting reaction mixture slurry is then digested in one to three stages for several hours at progressively increasing temperatures up to 200° C. with the injection of additional phosgene; and (3) the final solution of reaction products is fractionated to recover hydrogen chloride, unreacted phosgene and solvent for recycling, isocyanate product, and distillation residue for incineration."

In the conventional production of 4,4'-MDI, the amine which is phosgenated, 4,4'-methylene dianiline (4,4'-MDA), is produced by the condensation of aniline and formaldehyde. This reaction is not highly selective to 4,4'-MDA but leads unavoidably to the production of a mixture of dimers, trimers and higher oligomers, including dimers of other than the 4,4'-product.

A different process for the production of polymeric diisocyanates was recently announced by Atlantic Richfield Company. As described in *Chemical Week*, Nov. 9, 1977, pp. 57–58, the process comprises the steps of reacting nitrobenzene, carbon monoxide and an alcohol to form corresponding urethanes (alkyl phenyl carbamates). The reaction product is reacted with formaldehyde to produce a condensate which contains p,p'-methylene diphenyl dialkylcarbamate and higher oligomers. That product is, in turn, thermally split into the corresponding "polymeric diisocyanates" and alcohol, which is recycled. The set of reactions is reported to involve the use of high temperatures in the range between 100° and 200° C. in the first reaction step and between 200° and 300° C. in the decomposition step, and the reaction is reported to be non-selective, leading to a mixture of polymeric diisocyanates.

I am not aware of any process known in the prior art which is highly selective for the production of 4,4-MDI or its alkylidene homologs, nor of any cyclic process for selective production of 4,4'-MDI from formaldehyde and phenyl isocyanate such as that which is the subject of the present invention.

After the present process was developed, the following references were found in a search for disclosures related to the process:

Overall Process

No reference was found which suggests the overall process of this invention.

Condensation Reaction

No reference was found to the reaction of aldehydes or ketones with N-phenyl alkylcarbamates.

The only reference found which has any resemblance to the condensation step of my process in U.S. Pat. No. 3,059,021 to Prill. This patent is directed to the production of certain biologically active 1,1,1-trichloro-2,2-bis(carboalkoxyaminoaryl)ethanes as novel compounds by the reaction of chloral with an arylcarbamate, such as in the following reaction:

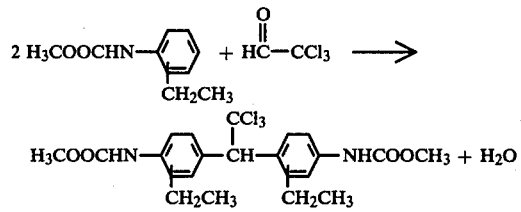

Exchange Reaction. No reference was found to the reaction of an isocyanate with a dicarbamate to yield the corresponding diisocyanate and carbamate.

A reference which resembles the reverse of the exchange reaction employed in the present invention is U.S. Pat. No. 3,345,395 to Muller et al. That patent is directed to the production of organic monoisocyanates by reacting a carbamic acid ester with an organic isocyanate having a boiling point above the isocyanate corresponding to the carbamic acid ester. The reaction is represented by the following equation:

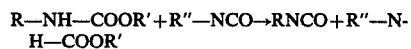

wherein R, R' and R" represent organic radicals. The isocyanate starting material may be a polyisocyanate.

In Examples 1–5 of the Muller patent, diisocyanates or polyisocyanates or their mixtures are reacted for hours at temperatures in the range between 170° and 240° C. and monoisocyanate products are recovered by distillation from the mixture.

SUMMARY OF THE INVENTION

The processes known for the commercial production of 4,4'-MDI, including the newly announced Atlantic- Richfield process, employ high temperatures and are not capable of producing 4,4'-MDI in high yield with high selectivity. The two-stage process of this invention is capable of converting phenyl isocyanate and formaldehyde in high yield and with phenomenally high selectivity to 4,4'-MDI and may be operated at temperatures as low as 60°–70° C., and hence with high energy efficiency.

The process of this invention is a cyclic process in which the only reagents are formaldehyde — or, if another alkylene bridge is desired, a higher aldehyde or a ketone — and phenyl isocyanate, and substantially the only products are 4,4'-MDI or a corresponding alkylidene diphenyl diisocyanate and water. Since 4,4'-MDI is the most desirable diphenyl diisocyanate of commercial interest, the invention will be discussed primarily in terms of production of 4,4'-MDI.

The process of this invention comprises a coupling reaction in which formaldehyde or other aldehyde or ketone is condensed with an N-phenyl alkylcarbamate with mild reaction conditions to produce the alkyl carbamate of 4,4'-methylene diphenyl diisocyanate in essentially quantitative selectivity, and a catalytic exchange reaction in which the latter is reacted with phenyl isocyanate to produce with extremely high selectivity and yield 4,4'-alkylidene diphenyl diisocyanate which is recovered as product and N-phenyl alkylcarbamate which is recycled to the coupling reaction.

BRIEF DESCRIPTION OF THE DRAWING

The sole FIGURE of the drawing is a schematic flow sheet of the process of this invention.

DESCRIPTION OF THE PREFERRED EMBODIMENTS

Starting Materials

Figure 1:
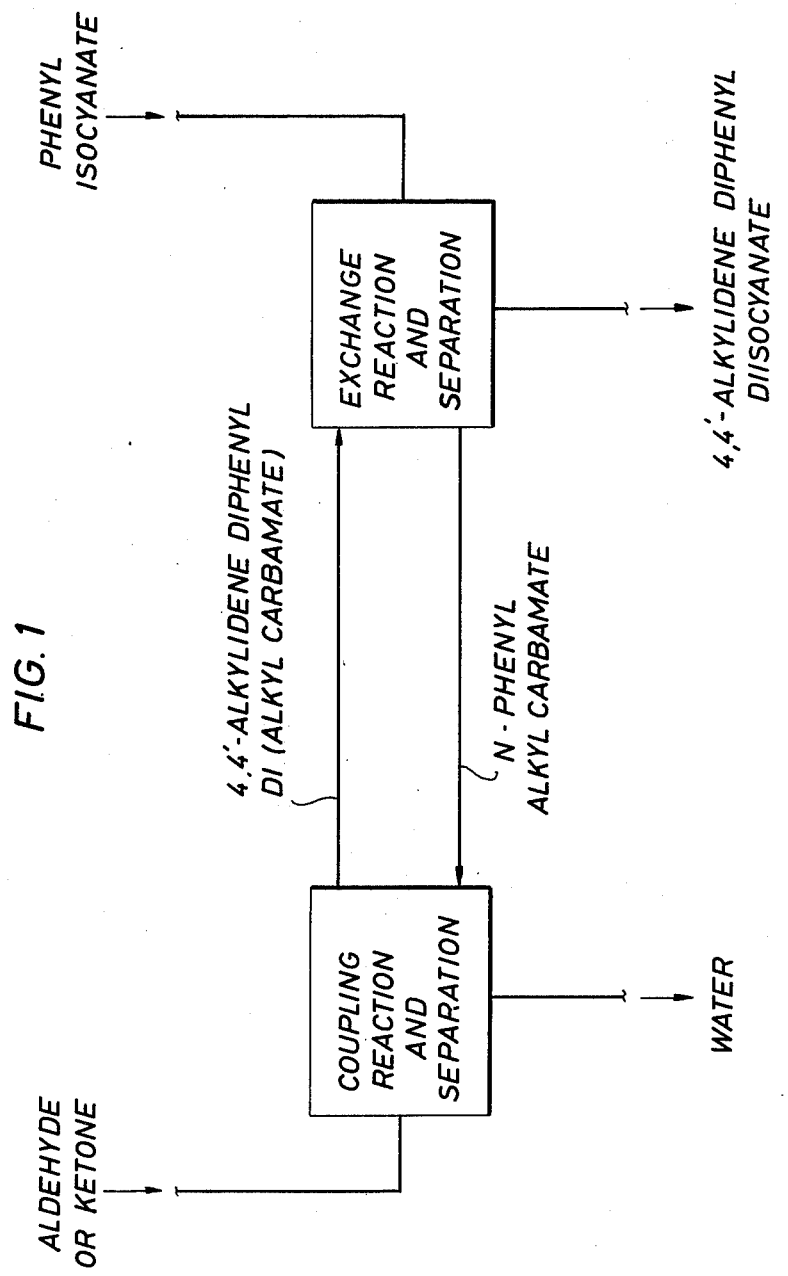

Formaldehyde (or other aldehyde or a ketone) and phenyl isocyanate are the only starting materials for this process. Small amounts of catalysts are employed in the coupling and exchange reactions.

Formaldehyde, used if 4,4'-MDI is the desired product, may be employed in the form of formalin (a 37% aqueous solution), but may also be charged in other forms, including its oligomers or polymers, e.g., trioxane or paraformaldehyde.

The reaction may also be carried out using higher aldehydes, e.g., acetaldehyde, propionaldehyde, etc. or ketones, e.g., acetone, methylethyl ketone, diethyl ketone, etc., to produce homologs of 4,4'-MDI having a different alkylidene group bridging the two benzene rings.

The phenylisocyanate starting material may be produced by a conventional method in which aniline and phosgene are reacted to yield phenyl isocyanate and HCl.

Phenyl isocyanate may also be produced by the reaction of nitrobenzene and carbon monoxide to yield phenylisocyanate and $CO_2$; see discussion of prior art in U.S. Pat. No. 3,719,699 to James D. McClure et al. This provides a route to 4,4'-MDI in which phosgene is not required as reagent.

The Overall Reaction.

The generic equation for the overall reaction according to this invention is as follows:

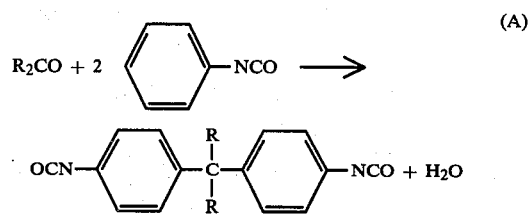

In this scheme, R represents hydrogen or any hydrocarbyl group which is not too bulky to permit the condensation reaction to proceed. Probably the only reaction which is of commercial interest is the production of 4,4'-MDI, which is represented by the following equation in which R of equation "A" represents hydrogen:

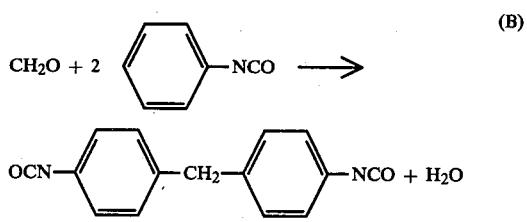

The process of this invention involves two reaction steps, namely, a coupling or condensation step and an exchange reaction step, as shown schematically in FIG. 1. The reactions, suitable reagents and conditions for these steps are as follows:

The Coupling or Condensation Reaction.

The generic equation for the coupling or condensation reaction is as follows:

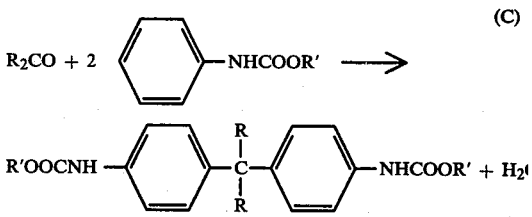

In this equation, R is as defined above and R' represents the residue of any suitable alcohol which is capable of reacting with phenylisocyanate to produce the corresponding carbamate and which does not contain any reactive groups that would interfere with either the exchange or the coupling reaction, such as, for example, aromatic rings, which could be subject to alkylation in the condensation reaction step. In a preferred mode of practicing the invention, R represents hydrogen and R' represents a lower alkyl group, e.g., a methyl, ethyl, n-propyl, isopropyl, or tert. butyl group.

The coupling reaction can, however, be effected with carbamates of a great variety of alcohols. For example, it has been successfully carried out with the carbamate of methanol, of 2(2-methoxyethoxy)ethanol and of a mixture of linear terminal alkanols of 12 to 15 carbon atoms. The following are representative alkanols, including substituted alkanols, whose carbamates may be employed in the coupling reaction:

Methanol; ethanol; n-propanol; isopropanol; linear alkanols $CH_3(CH_2)_n-CH_2OH$ where n is 1-12;

branched alkanols of 1–12 carbon atoms, provided they are not so bulky as to interfere with the reactions; methoxy-, ethoxy- and methoxyethoxyalkanols; and alkanols having a substituent group such as halogen, ester, amide or alkyl sulfide.

As is evident from the general reaction scheme, the R' component of the carbamate group circulates in the process. Once the starting amount of N-phenyl alkylcarbamate has been introduced, the only additional amount required is that required for makeup of amounts lost from the process. A suitable carbamate group may be selected to facilitate the method chosen for carrying out the separation steps which follow the exchange reaction and the coupling reaction.

The coupling reaction is suitably carried out under mild condensation reaction conditions. In general, the coupling reaction is carried out in a polar solvent, e.g., water, in the presence of a Bronsted acid (See *Chem. Rev.* 5, 231 (1938)), which is capable of giving up a proton in the polar solvent employed in the system. The reaction is suitably carried out at a moderately elevated temperature below 100° C.; about 60° C. was found to be a suitable temperature. In an illustrative condensation reaction, a mixture of N-phenyl methylcarbamate and a 37% aqueous solution of formaldehyde was agitated with zinc chloride while saturated with hydrogen chloride, at a temperature of 60° C. Within about 20 minutes the mixture turned water-clear and then yielded a chalk-white solid in a sudden precipitation. The solid, after washing, was found to be substantially pure 4,4'-methylene diphenyl dimethylcarbamate.

Related methods of carrying out the coupling step will be evident to the skilled organic chemist. Numerous acidic condensation catalysts are known, including acidic resins, which may be attractive in some cases. Methods known to be suitable for the condensation of formaldehyde with aniline should generally be suitable for the condensation of formaldehyde with N-phenyl alkylcarbamate. For example, see references cited in the paper by E. C. Wagner, *J. Org. Chem.*, 59, 1862 (1959).

The generally preferred solvent for the coupling reaction is water. The solvent should be non-aromatic. Suitable non-aromatic organic polar solvents may be selected from ethers, such as tetrahydrofuran, diethyleneglycol dimethylether(diglyme) and other oligomeric ethers; alcohols, such as alkanols of 1–10 carbon atoms; halogenated hydrocarbons, such as chloroform; acetonitrile and the like.

The Exchange Reaction.

The generic equation for the exchange reaction is as follows:

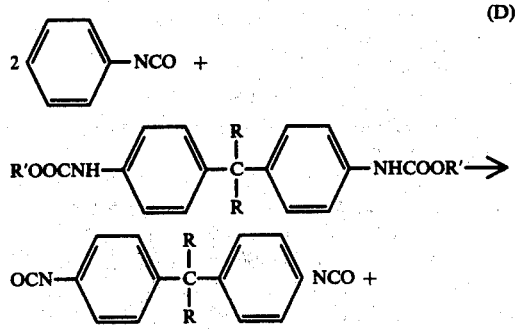

(D)

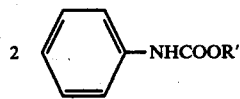

In this equation, R and R' are as defined above.

In the exchange reaction, the phenyl isocyanate is one of the reactants charged to the overall process and the dicarbamate is the product of the coupling reaction. When carried out as described below, the exchange reaction produced 4,4'-MDI in high yield and high purity, the second product being an N-phenyl alkylcarbamate which is recycled as one of the reagents to the coupling reaction.

The exchange reaction can be considered as being based on two reactions which take place concurrently, namely, the equilibrium between the dicarbamate and the respective diisocyanate and alcohol according to the following equation:

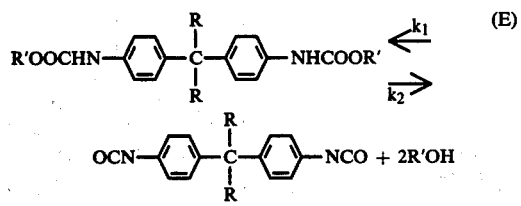

(E)

and the reaction of phenyl isocyanate with the resulting alcohol according to the following equation:

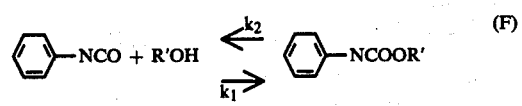

(F)

In the absence of catalyst, reaction E does not reach dynamic equilibrium at the temperatures preferred for use in the invention. The dicarbamate is a very stable compound and is not converted to the diisocyanate and alcohol in any measurable or significant amount. Therefore, the presence of phenylisocyanate with the dicarbamate causes no appreciable change in the concentration of 4,4'-MDI in the mixture in the absence of a catalyst. In the presence of a suitable catalyst, however, a dynamic equilibrium is established. Reaction E proceeds very fast in the presence of a suitable catalyst and goes to equilibrium. The steady state concentrations of diisocyanate and alcohol in reaction E are unaffected by the action of the catalyst and are, in this system, trace amounts dictated by the equilibrium constant $K = k_1/k_2$. This equilibrium can be displaced to the right by withdrawing the alcohol from the system. This is achieved by introducing phenyl isocyanate into the reaction. A suitable catalyst will couple the equilibrium of reactions E and F and establish a new equilibrium in which the concentration of 4,4'-MDI increases indirect proportion to the concentration of added phenyl isocyanate. The alcohol of reactions E and F, which is an intermediate product that is not present in a concentration detectable by standard analytic techniques and is never isolated, does not distinguish between the diisocyanate and the phenyl isocyanate and thus forms phenylalkylcarbamate according to reaction F. A compound of mixed functionality, the monoalkylcarbamate of 4,4'-MDI, will also be present in the exchange mixture. Complete exchange of functionality can be achieved in the exchange reaction system by withdrawing either the phenyl alkylcarbamate or the diisocyanate from the reaction system, as for example, by causing pure 4,4'-MDI to crystallize out of the reaction mixture.

The exchange reaction is catalyzed by only certain catalysts which are suitable for catalyzing the addition of isocyanate to an alcohol.

The activity of exchange catalysts were tested on solutions of toluenediisocyanate and N-phenyl methylcarbamate and of phenyl isocyanate and the dimethylcarbamate of 4,4'-MDI. Toluenediisocyanate is not a reactant in the process of this invention; however, it is a suitable reactant for testing the catalytic effectiveness of potential catalysts for the exchange reaction.

Although amines are reported to catalyze the addition of isocyanates to alcohols, it was found that two amines tested, triethylamine and 1,4-diazabicyclo(2.2.2)-octane, the latter known to be an outstanding catalyst for reaction F, catalyzed a rapid polymerization of the reagents to the exclusion of exchange.

Many, but not all, tin compounds proved to be quite active and clean exchange catalysts. Tetravinyltin, tetramethyltin and stannous ion on silica gel all proved inactive. Tributyltin hydride, tin tetrachloride and trimethyltin chloride were all active and clean exchange catalysts. Surprisingly, various supported stannic compounds proved to be active and clean exchange catalysts. Silica gel and porous glass, saturated with $SnCl_4$ and then washed with benzene and acetone, were active. The activity appeared to be genuinely heterogeneous; there was no evidence of leached $SnCl_4$ in the experiments. Sodium stannate, dry-impregnated on $Al_2O_3$, and a combination of a metal stannate and copper on alumina, were also active and selective exchange catalysts.

Zinc chloride proved entirely inert, causing no reaction whatsoever.

The exchange reaction proceeds smoothly in the presence of a catalytic amount of an effective catalyst at temperatures in the range from 30° to 100° C. A preferred temperature range if from 60° to 70° C. Complete equilibrium is reached in as little as 20 minutes. As stated above, completion of the reaction to produce the diisocyanate in one reaction stage requires the progressive removal of the diisocyanate from the reaction mixture.

The exchange reaction does not require use of an extraneous solvent. Phenylisocyanate is a liquid at the reaction conditions and acts as solvent. The dicarbamate in which R' is methyl is, however, not very soluble in phenyl isocyanate, and accordingly, the exchange reaction mixture, in that case, is a slurry. Dicarbamates of higher alcohols may lead to a fully liquid exchange reaction mixture.

In a test of the selectivity of the exchange reaction, a solution of 30 grams of N-phenyl methylcarbamate, 36 grams of toluene diisocyanate and 55 grams of chlorobenzene as internal standard was prepared and their respective %w K factors determined by hydrogen flame gas-liquid chromatography (GLC). Ten ml of this solution and 1 ml dibutyltin dilaurate, heated at 70° with stirring, gave a water-white solution. Complete equilibration was reached in under 20 minutes. There was no change in the respective components with continued heating at 70° for 1.5 hours. The equilibrated solution, treated with an excess of methanol yielded the theoretical amount of N-phenyl methylcarbamate. Thus the phenyl isocyanate was recovered in 100% yield. An equal sample of the original standard solution was also treated with methanol and its product compared to that of the exchange product. The GLC spectra were the same and thin layer chromatography on both $SiO_2$ and $Al_2O_3$ showed only two identical spots, N-phenyl methylcarbamate and the dimethylcarbamate of toluene diisocyanate.

In the above experiment, the chlorobenzene was added to calibrate the response factor of the GLC and then used as internal standard to obtain a reliable material balance by GLC. It is chemically inactive in the exchange reaction.

Product Recovery

The dicarbamate product of the coupling reaction step (reaction C) is one of the reactants in the exchange reaction step (reaction D). The solvent and catalyst employed in the coupling step may, however, interfere in the exchange reaction. Accordingly, it is generally necessary to separate and wash the dicarbamate, for example, by recovering it as a solid and washing it with a suitable solvent which does not interfere in the exchange reaction.

In the production of 4,4'-MDI, the reaction mixture in the exchange reaction zone consists of phenylisocyanate, phenyl alkylcarbamate, 4,4'-MDI carbamate, 4,4'-MDI and catalyst.

In a system employing a solid, heterogeneous catalyst, the components are readily separated by fractional distillation, suitably at reduced pressure. If a homogeneous catalyst is employed, it is selected so that its volatility permits its removal from the other mixture components in the distillation step.

Experimental data illustrating the steps of the process of the invention have been cited in the above discussion. The following embodiment illustrates a method of practicing the process.

Illustrative Embodiment

In a stirred reactor, 100 parts by weight (abbreviated pbw; equal to 0.66 molar parts) of N-phenyl methylcarbamate was combined with 10 pbw of formaline (33% aqueous formaldehyde solution, containing 0.124 molar parts HCHO) and 13 pbw of zinc chloride, under a stream of gaseous HCl, to keep the mixture saturated with HCl. The mixture was heated, with stirring, to 60° C. It turned clear after about 20 minutes and yielded a white solid. At this point, the mixture had the appearance and consistency of ice cream. To facilitate handling and to serve as internal standard for GLC analysis, 58 pbw of chlorobenzene was added. The product mixture was then washed twice with about 100 pbw portions of water, twice with similar portions of aqueous sodium bicarbonate and again with water. The white, solid crude product was recovered by filtration. By GLC and TLC analysis and by comparison with a product synthesized from sure 4,4'-MDI and methanol, it was shown to be a mixture of pure methyl carbamate of 4,4'-MDI and the starting material, N-phenyl methylcarbamate.

In an alternative condensation reaction, 100 pbw (0.66 molar parts) of N-phenyl methylcarbamate was combined with 17.8 pbw (0.22 molar parts HCHO) of formalin solution and 17.8 pbw of 37% aqueous HCl (0.178 molar parts HCL) and stirred for 10 minutes at 60° C. Two liquid phases resulted. Addition of dry HCl and heating to 70° C. with stirring resulted in a thick suspension of solid material. Then about 200 pbw of chlorobenzene was added to facilitate handling and as internal standard for GLC. The product was washed sequentially with sodium bicarbonate and sodium hydroxide. The water layer was separated and the white solid filtered from the organic layer. Again, the sole reaction product was the dimethylcarbamate of 4,4'-MDI.

The washed solid product from the coupling reaction may be concentrated, if desired, by appropriate means to remove the unreacted starting materials, or it may be conveyed directly to the exchange reaction zone.

One hundred pbw (0.318 molar parts) of the washed, acid- and base-free solid dimethylcarbamate of 4,4'-MDI, prepared as above, is conveyed to the exchange reaction zone, where it is combined in a stirred reactor with 1200 pbw (10.08 molar parts) of phenyl isocyanate from an extraneous source. A small amount of the dicarbamate dissolves in the phenyl isocyanate. The rest remains as slurried solid. Silica gel saturated with tin tetrachloride (300 pbw) is added as catalyst and the reaction mixture is heated to and maintained at 70° C. A slip stream of the reaction liquid (after separation of solids) is continuously withdrawn and passed to a fractionation zone, where it is distilled under vacuum, e.g., at 3mm mercury pressure. Unconverted phenylisocyanate, boiling at 30° C., is taken overhead and returned to the exchange reaction zone. N-phenyl methylcarbamate, boiling at 96°–97° C., is taken as an intermediate product and is recycled to the coupling reaction zone; sure 4,4'-MDI (boiling at 166° C.) is recovered as a distillate fraction as the sole product of the process, requiring no further purification; and the monoalkyl and dialkyl carbamates of MDI remain in the bottoms fraction, which is then returned to the exchange reaction zone.

What I claim is:

1. Process for the selective production of 4,4'-alkylidene diphenyl diisocyanate, consisting essentially of the steps of
    (1) condensing a compound R₂CO, wherein R represents hydrogen or any hydrocarbyl group which is not too bulky to permit the condensation reaction to proceed, with a compound

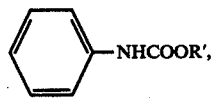

wherein R' is the residue of an alcohol which is capable of reacting with phenyl isocyanate to produce the corresponding carbamate and which does not contain any reactive groups that interfere with the reactions, of steps (1) and (2), under mild condensation reaction conditions in a polar solvent, to yield the dicarbamate of formula

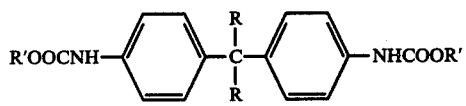

and water;
    (2) reacting said dicarbamate with phenyl isocyanate in the presence of a catalytic amount of an effective exchange reaction catalyst under mild reaction conditions to yield the corresponding diisocyanate and

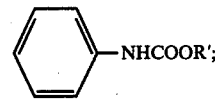

and
    (3) continuously removing and recovering said diisocyanate from the exchange reaction mixture.

2. Process for the selective production of 4,4'-methylene diphenyl diisocyanate, consisting essentially of the steps of
    (1) condensing formaldehyde with a compound

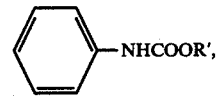

wherein R' is the residue of an alcohol which is capable of reacting with phenyl isocyanate to produce the corresponding carbamate and which does not contain any reactive groups that interfere with the reactions, of steps (1) and (2), under mild condensation reaction conditions in a polar solvent, to yield the dicarbamate of formula

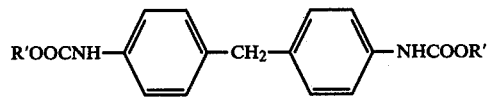

and water;
    (2) reacting said dicarbamate with phenyl isocyanate in the presence of a catalytic amount of an effective exchange reaction catalyst under mild reaction conditions to yield 4,4'-methylene diphenyl diisocyanate and

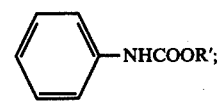

and
    (3) continuously removing and recovering said diisocyanate from the exchange reaction mixture.

3. The process of claims 1 or 2 wherein R' is selected from the group consisting of alkyls of 1–12 carbon atoms, alkoxy-substituted alkanols and alkyls substituted with non-reactive functional groups.

4. The process of claims 1 and 2 wherein said reaction step (1) is conducted in water as solvent in the presence of an acidic condensation catalyst at a temperature below 100° C., and said reaction step (2) is conducted at a temperature below about 100° C.

5. The process of claims 1 or 2 wherein said diisocyanate is continuously removed from the reaction mixture of reaction step (2) by crystallization.

6. The process of claims 1 or 2 wherein said diisocyanate is continuously removed from the reaction mixture of reaction step (2) by fractional distillation under reduced pressure.

7. The process of claim 2 wherein said reaction step (1) is conducted in water as solvent in the presence of a Brønsted acid condensation catalyst at a temperature below 100° C., and said reaction step (2) is conducted in the presence of a tin compound as catalyst at a temperature below about 100° C.

8. The process of claim 7 wherein said condensation catalyst is a combination of zinc dichloride and HCl and said exchange reaction catalyst is selected from the group consisting of tributyltin hydride, tin tetrachloride, trimethyltin chloride, tin tetrachloride supported on a porous siliceous support, sodium stannate supported on alumina, and a combination of sodium stannate and copper on alumina.

9. The process of claims 7 or 8 wherein said diisocyanate is continuously removed from the reaction mixture of reaction step (2) by crystallization.

10. The process of claims 7 or 8 wherein said diisocyanate is continuously removed from the reaction mixture of reaction step (2) by fractional distillation under reduced pressure.

* * * * *